United States Patent [19]

Sisti et al.

[11] Patent Number: 4,526,686
[45] Date of Patent: * Jul. 2, 1985

[54] APPARATUS FOR CHROMATOGRAPHIC SAMPLE INJECTION

[75] Inventors: Giorgio Sisti, Milan, Italy; Sorin Trestiano, Brussels, Belgium; Ermete Riva, Merate, Italy

[73] Assignee: Carlo Erba Strumentazione S.p.A., Rodano, Italy

[*] Notice: The portion of the term of this patent subsequent to Sep. 20, 2000 has been disclaimed.

[21] Appl. No.: 533,899

[22] Filed: Sep. 20, 1983

Related U.S. Application Data

[63] Continuation-in-part of Ser. No. 304,780, Sep. 23, 1981, Pat. No. 4,405,344.

[30] Foreign Application Priority Data

Sep. 30, 1980 [IT] Italy ............................... 25018 A/80
May 4, 1981 [IT] Italy ............................... 21504 A/81

[51] Int. Cl.³ .............................................. B01D 15/08
[52] U.S. Cl. ................................ 210/198.2; 210/198.3; 55/197; 55/386
[58] Field of Search ................. 210/658, 198.3; 55/67, 55/197, 386

[56] References Cited

U.S. PATENT DOCUMENTS

| 3,366,149 | 1/1968 | Taft et al. ......................... 55/67 X |
| 3,523,890 | 8/1970 | Stahl .................................... 210/658 |
| 3,667,917 | 6/1972 | Brandt ................................. 210/658 |
| 4,383,839 | 5/1983 | Sisti et al. ............................ 55/67 |
| 4,405,344 | 9/1983 | Sisti et al. ............................ 55/67 |

OTHER PUBLICATIONS

Gas Phase Chromatography, vol. II by Kaiser, Butterworths, Washington (1963), pp. 59-62.
Journal of Chromatography Library, vol. 9, Zlatkis and Kaiser, Editors, Elsevier Scientific Pub. Co. (1977), pp. 85-94.
Journal of High Resolution Chromatography & Chroma. Communications, vol. 2, by Grob, Jr. and Neukom. (Sep., 1979), pp. 563-569.
Bulletin 106, Rheodyne, Inc. California, 1979.
"Operating Instructions for Model 7010 Sample Injection Valve," Rheodyne, Inc. California, 1981.

Primary Examiner—John Adee
Attorney, Agent, or Firm—Millen & White

[57] ABSTRACT

An apparatus for controllably and reproducibly introducing, small amounts of a liquid sample into chromatographic systems, especially high resolution gas chromatographic systems with cold injection, thin-layer chromatographic systems and high resolution liquid chromatographic systems, in order to obtain sampling extremely reduced in volume and presenting maximum reliability and reproducibility, uses a sample container having a pipette-like or nozzle-like outlet neck of very small diameter. The liquid placed in the container is submitted to at least one pressure pulse which is controlled in duration and/or amplitude in order to determine emission of a corresponding and controlled quantity of liquid from the outlet neck.

9 Claims, 9 Drawing Figures

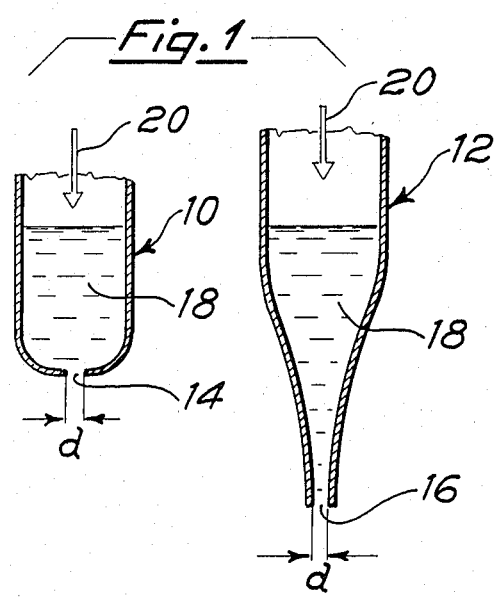
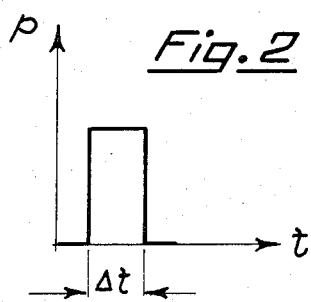
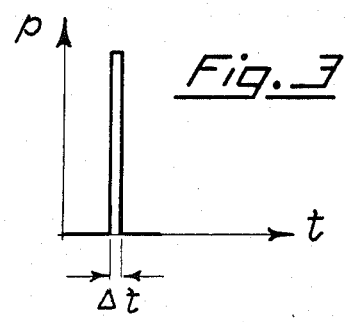
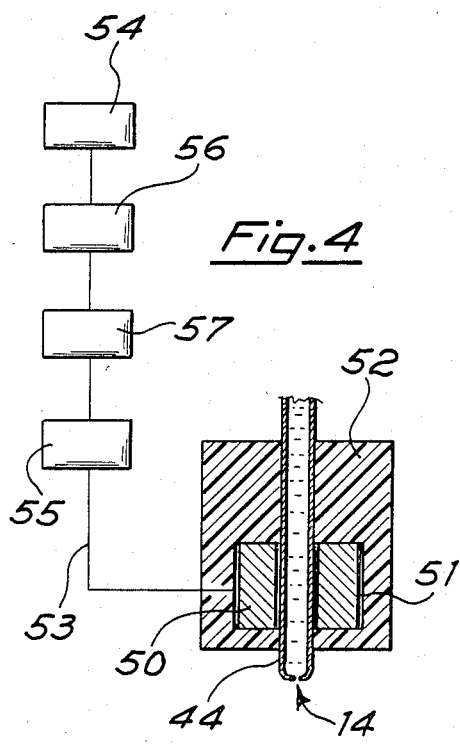
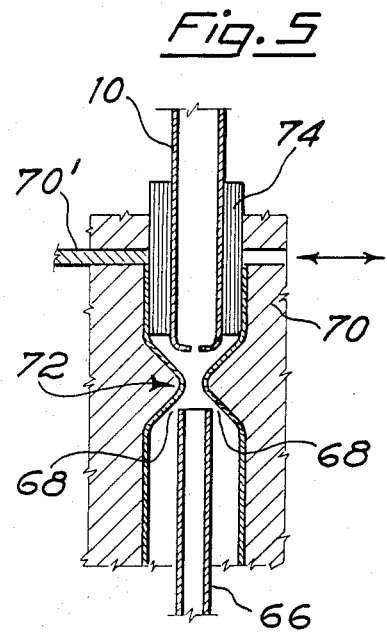

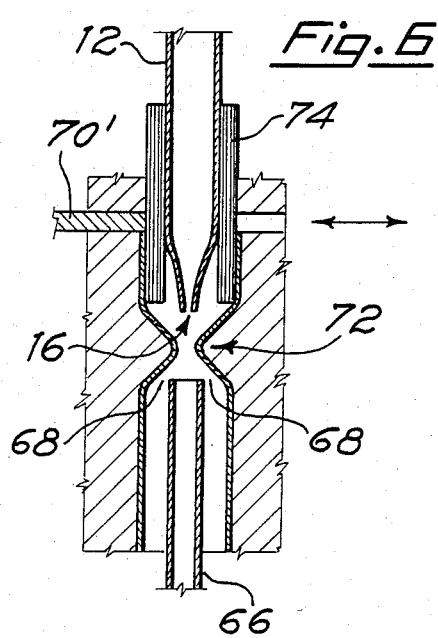
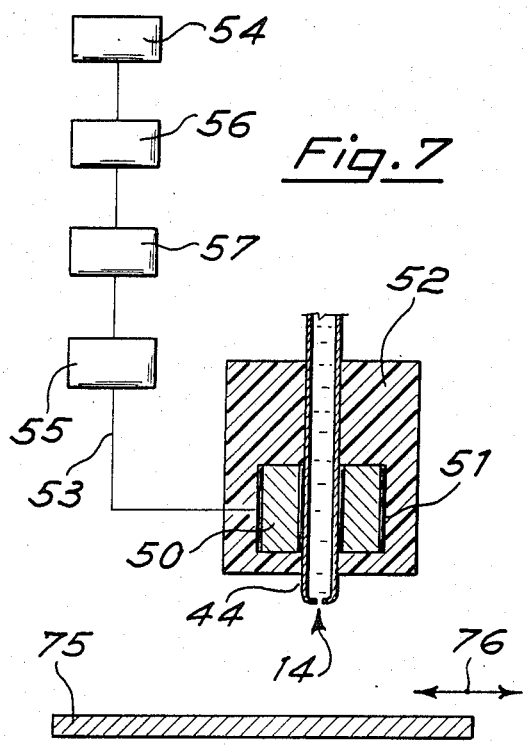
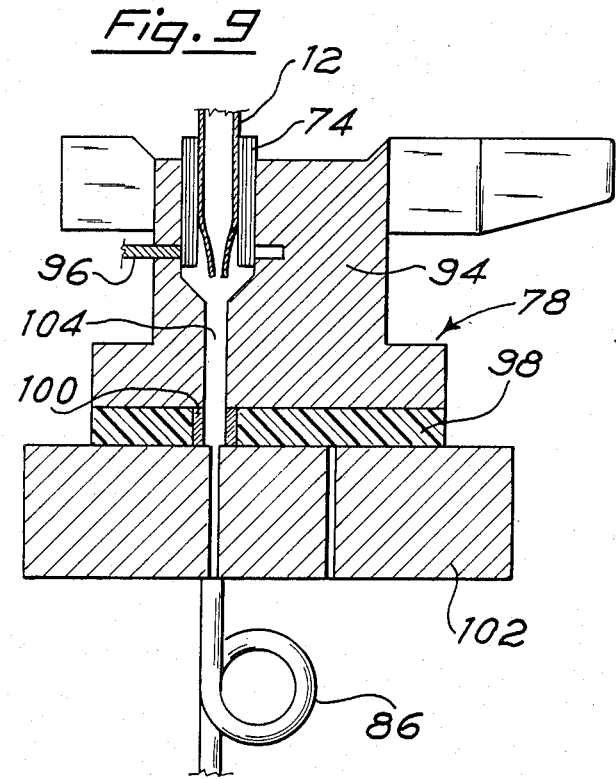
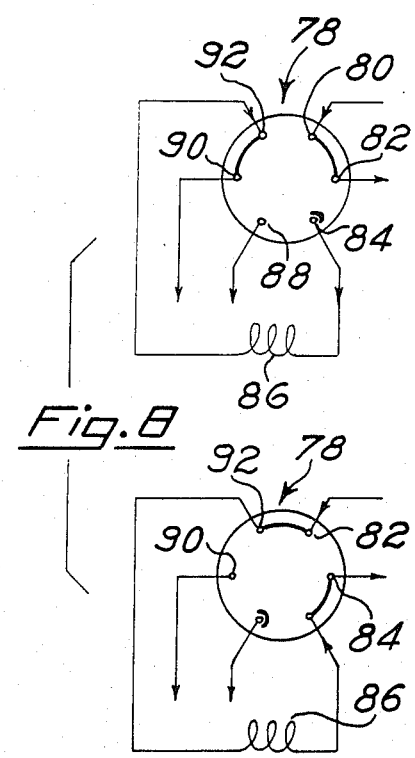

APPARATUS FOR CHROMATOGRAPHIC SAMPLE INJECTION

This application is a continuation-in-part of U.S. Ser. No. 304,780, filed Sept. 23, 1981, now U.S. Pat. No. 4,405,344 issued Sept. 20, 1983, the disclosure of which is incorporated herein by reference in its entirety.

BACKGROUND OF THE INVENTION

1. Field of the Invention

The present invention relates to an apparatus to perform sampling in chromatographic systems with very small amounts of liquid sample, said apparatus being particularly applicable to high resolution gas chromatographic systems with cold injection, using capillary or micropacked columns, to high resolution liquid chromatographic systems, or to thin-layer chromatographic systems. Use of this apparatus makes it possible to perform controllable and reproducible sampling on very small amounts of sample, with values unattainable through the techniques usually employed for liquid sampling in chromatographic systems and particularly using micro-syringes or pipettes.

2. Description of the Prior Art

For all chromatographic systems problems arise for injecting in a volumetrically controlled and reproducible way very small quantities of sample into a chromatographic system. In gas chromatographic systems with cold injection, when a cold on-column or a cold splitless injection (according for example to the method described in U.S. Pat. No. 4,383,839) are used, it has been foreseen the necessity to inject small sample amounts in order to reduce or eliminate the problems created by a high content of diluting solvent (flooding effect, partial solvent trapping effect etc). But also when cold split injection is considered a small sample is advantageous due to the fact that it requires a lower splitting ratio and then errors or discriminations generally arising at high splitting ratios are avoided (see for example K. Grob Jr. and H. P. Neukom—Journal of H R C & C C Vol. 2 September 1979; 563–569). The modern tendency to use small bore capillary columns also requires the injection of small sample sizes unachievable with the dosing systems used today.

In thin-layer chromatography the use of very small sample volumes is especially required (A. Zlakis and R. E. Kaiser: HPTLC Elsevier Scientific Publishing Company—Institute of Chromatography Bad Dürkheim 1977; 85–94).

Both these injection systems use syringes, microsyringes or pipettes as will be described later on.

The high resolution liquid chromatography systems usually use injectors with sampling valves having a loop wherein the sample is loaded for instance by means of a syringe. The loop is then connected with the column and with a source of eluting liquid solvent under pressure, to force the sample through the column.

In this case too, small volumes of sample are preferred and often imposed by the characteristic of the column. The modern trend is the use of microbore and capillary packed columns. Of course in all described injection systems it is necessary to obtain not only small sample quantities, but small sample quantities exactly measured and injected in a perfectly reproducible manner.

The microsyringes used in chromatography are generally of the type with calibrated body (capable of sampling amounts ranging from 0.2 to 10 microliters) or of the type with calibrated needle, where the piston penetrates into the needle. The latter microsyringes are capable of handling smaller quantities of samples, in a reliable and reproducible way, but only within certain limits, in particular with lower limits of about 100–200 nanoliters. Below this limit, the high surface tension of the liquid and the relatively reduced speed of the piston movement do not allow the drop, which has formed at the needle end, to fall from it, considering the reduced diameter of the outlet nozzle of the needle. Precision is moreover negatively affected by poor sealing between piston and calibrated needle. Another known system is the sampling system commonly used in the laboratory and named "pipette system", in which a calibrated tubing is filled with a liquid to be transferred by filling the pipette due to capillary forces or by sucking it into the tubing. The liquid amount placed in the tubing is retained in the tubing by the capillary forces or by closing one end when liquid aspiration has been carried out. Then, an injection of the liquid is made by opening said end or pushing the liquid by the carrier gas. This sampling method or transfer method of determined amounts of liquid is well known and has been used in gas chromatography too, but however only for quantities usually measurable in a rather rough way. The literature reports a lower limit of 25–50 nanoliters (see R. Kaiser—Gas Phase Chromatography—Vol. I pp. 90-9-5—Butterworths 1963—London) but thise limits are difficult to reach and anyhow require small tubes filled exclusively due to capillary forces. This implies that the volume of liquid injection is difficult to control and reproduce.

Therefore it can be considered that, of course according to the nature of the liquid substance to be sampled, a lower limit exists, generally between 50 and 200 nanoliters, below which it is not possible to go in reliable and reproducible manner using microsyringes or micropipettes.

The above mentioned quantitive limitations, however, are such that the operator is often forced to perform accessory operations imposed by the relatively high quantities of sample that has to be introduced into the chromatographic system. In particular, sometimes the sample must be diluted in a dilution ratio which is oftern very high (of the order of 1:10000 or more), with an operation which may involve difficulties in the exact analytical determination of the sample and in that it can introduce discriminations or variations in the sample original conditions.

In other cases, a splitting operation is necessary, that means the elimination of a high percentage of the quantity fed to the injector, before its introduction into the column, which operation may involve even higher risks of discriminations especially as above said, with hight split ratios. Between the known injection systems, Kaiser, *Gas phase Chromatography*, Vol. 11, pags. 59–62, discloses methods and apparatus for sample injection into gas chromatographic systems. Two particular types of injection devices are shown in FIGS. 26 and 27 of the reference. Both the injection devices described by Kaiser are versions of a micropipette type device. They are designed to be filled by capillarity with an uncontrollable quantity of liquid, which is then injected in its entirety into the evaporation area of sampling system. Sample sizes are in tenth of microliter range, roughly two orders of magnitude larger than the size of sample which can be obtained according to the present invention.

The device of FIG. 27 of Kaiser is quite similar to that of FIG. 26. Again, the sample size is determined in the filling operation. This device is also capable of handling solids which can be melted to give a homogeneous liquid.

Taft et al., U.S. Pat. No. 3,366,149, discloses a system for injecting samples which is particularly useful for injecting larger samples for preparative gas chromatography. In this system, a constant pressure is maintained on the surface of a liquid in a sample container communicating with a heater through a valve. The valve is controlled by a solenoid pulser, which operates to open the valve for a controllable time interval.

This reference is relied upon for its showing of pulse flow. However, the pulse operates on the valve, and the reference does not show a pressure pulse operating on a liquid whose flow is not constrained by a valve. Rather than operating to inject samples in the picoliter or nanoliter range, the system of Taft operates to inject samples of the order of milliliters. The system is not designed to deal with very small sample sizes, and operates on an entirely different principle.

It will be seen from the above comparison that the prior art sample injection devices operate by controlling sample size in the filling step and injecting the entire contents of the filled injection system using pressure in a different way from the way in which it is employed in the present invention. Even a combination of the cited references would only lead the skilled art worker to a pipette of the type shown in FIG. 26 or 27 of Kaiser which, however, is actuated by a pulsed valve. This type of device is typical of a titration burette which commonly delivers minimum sample quantities of 0.1–0.2 milliliters, and is unable to deliver samples in the picoliter or nanoliter volume range.

OBJECTS OF THE INVENTION

Accordingly, an object of the invention is to provide an apparatus making it possible to perform sampling in chromatographic systems with small amounts of liquid sample; for instance from 10 picoliters to 50 nanoliters, in a reproducible way under the same conditions and sample type.

Another object of the present invention is to provide an apparatus, wherein the volumetric dosage of the substance injected into the chromatographic system is performed with the maximum of reliability, precision and reproducibility, during the injection stage itself.

SUMMARY OF THE INVENTION

According to the invention an apparatus is provided for volumetrically controlled and reproducible injection of small quantities of liquid sample into a chromatographic system comprising, in combination with an injection device for a chromatographic system:

a sample container having a volume grater than a desired liquid sample volume and having a pipette—or nozzle-shaped neck at its outlet, terminating in an opening with a diameter of 1–100 μm;

positioning means for operatively positioning said sample container in a sample injection device of a chromatographic system, for injection of a sample through said outlet opening; and pulse means communicating with said container for applying to a liquid inside the container at least one pressure pulse of controlled amplitude and duration, and ending in an abrupt pressure drop; wherein said pulse means comprises at least one transducer capable of producing at least one pressure pulse of high amplitude and short duration in the sample container; a pulse source for exciting said transducer; and means for adjusting at least one of the amplitude or the number of the pulses.

Therefore, by such apparatus, it is now possible to carry out sampling of extremely reduced quantities of liquid, using a container which can be of the substantially traditional type, except for the outlet neck, to which a device can be applied which allows to create said pressure pulse, in such a way that the sample drawing and eventual washing of the container can be performed with extremely simple and traditional systems and means, through being possible to perform said samplings with extremely reduced quantities.

According to the invention said pulse means may comprise the application, to the container body and/or to means mechanically connected with the same, of a mechanical pulse, obtained with a piezoelectric system, a magnetostrictive system or other similar system, which determines an extremely high and extremely quick pressure increase in the liquid and allows the detention of short duration rectangular pulses.

BRIEF DESCRIPTION OF THE DRAWINGS

FIG. 1 is an enlarged view, in axial section, showing possible shapes of the outlets of containers for samples to be used according to the invention.

FIGS. 2 and 3 are examples of possible pressure pulses used in the method and equipment according to the invention to perform desired sampling.

FIG. 4 diagrammatically shows an embodiment of apparatus for sampling by means of pressure pulses obtained with a piezoelectric system.

FIGS. 5 and 6 are diagrammatic views of possible positions of the sample container in use with a cold split-splitless injection.

FIG. 7 is a diagrammatic view showing the use of the apparatus in thin layer chromatography.

FIGS. 8 and 9 are diagrammatical views showing the use of the apparatus in liquid chromatography with a known sample loading device.

DESCRIPTION OF THE PREFERRED EMBODIMENTS

The invention relates, as already said, to an apparatus for sampling, in chromatographic systems, of liquid samples, said apparatus being particularly applicable to laboratory gas chromatography with cold split or splitless injection, in high resolution liquid chromatographic systems or in thin-layer chromatographic systems. This apparatus is capable of allowing injection of a very small liquid sample sizes compatible with the requirements of high resolution chromatographyc sistem, without need of dilution, as it is necessary in traditional method and apparatus to obtain a precise dosage of the injected sample. Although larger amounts can also be injected, the apparatus which will be illustrated is particularly suitable for the injection in a realiable and reproducible way, of liquid samples in quantities ranging between 10 picoliters and 50 nanoliters, i.e. amounts so small that they could not be handled with the previously employed systems.

The apparatus of the invention is based on the use of a container for the liquid sample which has a volume greater than that of the sample to be injected, said container being made of any suitable material, for instance glass, metal, fused silica or any other material, and having a pipette shape, a syringe needle shape or any other suitable shape.

The essential condition is that said container, as indicated by 10 or 12 in FIG. 1, presents a neck defining an outlet having a maximum size (a diameter d in this specific case) ranging from 1 to 100 μm, preferably between 1 and 30 μm. Said neck can be nozzle-shaped, as indicated by 14 in FIG. 1, and therefore has a preferred neck diameter d from 10 to 30 μm, or micropipette-shaped, as indicated by 16 in the same FIG. 1, with a preferred diameter d from 1 to 20 μm. The container, 10 or 12 as illustrated in FIG. 1, can be filled by the usual methods, for instance by means of a syringe, by gravity, or in any way whatsoever, with a quantity of liquid 18 which is greater than the volume that is required to flow from the neck 14 or 16 to be analyzed in the chromatographic system. Once the container 10 or 12 has been fed with the sample 18, it is necessary to check, especially in the case of the container 12 with a pipette-like end, that the liquid goes as far as to reach the neck 14 or 16, forming a meniscus therein. Under these conditions, taking into account the reduced size of the neck, the surface tension of the liquid prevents the latter from flowing out of the neck, forming drops, this obviously provided that the neck 14 or 16 does not touch foreign bodies, which may help the liquid to flow outside the container.

Once the feeding of the container 10 or 12 as previously indicated has been carried out, pressure on the liquid 18 is exerted directly or indirectly as schematically shown by the arrows 20 in FIG. 1 to eject a mesured amount of liquid 18 through the neck 14 or 16. Said pressure is controlled in amplitude and in time as indicated in FIGS. 2 and 3, keeping into consideration that the liquid amount ejected depends both on the amplitude, namely the value of the pulse pressure, on the duration of the pulse itself and on the number of pulses.

As it can be seen from FIGS. 2 and 3, the pulse has a step configuration and it is very important that the downwards section of same, namely pressure return to zero, be placed vertically as much as possible in order to avoid, during this stage, in correspondence to the neck 14 or 16, the formation of a drop which will remain in position, thus completely altering any measuring of the injected sample. In the case of FIG. 2, the pressure pulse is a long duration pulse and reaches a value which must be in any case higher than that necessary to overcome the surface tension of the liquid in correspondence with the neck 14 or 16. In relation to the pressure value, the duration Δt of the pulse is chosen, variable from about a millisecond to about a second, in order to obtain the desired quantities of ejected liquid.

Alternatively, it can obsiously be possible to emit several pulses having lower duration. However, for an exact reproducibility of sampling, it is very important to reduce to the minimum the dead space, that is the gas volume on which each pressure pulse acts.

The situation illustrated in FIG. 3 is the one that occurs in case of a pressure pulse exerted by means of magnetostriction, or piezoelectricity. In this case, the time Δt is extremely reduced and corresponds to the resonance frequency of the laminations forming the magnetostriction device or to the frequency of the piezoelectric material, ranging from 10 to 100 KHZ, while a certain regulation of the quantity emitted at each pulse can be performed by varying the amplitude of the electric pulse given to the device and consequently the pulse pressure value given to the liquid, said pressure value being in any case of one or several orders higher than that necessary in the pneumatic case.

The sampling apparatus illustrated in FIG. 4 operates with a piezoelectric system which, in that part including the element for formation and emission of the jet of drops, is substantially configured like an inkdrop printing device, of the "jet on demand" type, known in itself. It essentially comprises a container 44, for example but not necessarily with a cylindric shape, made of glass or fused silica, ready to be filled in its lower section with the sample to be injected into the column, for instance introduced through the upper section thereof.

The container 44 ends in its lower section with a calibrated nozzle 14, as previously indicated, through which the liquid jet of sample is emitted. Under atmospheric pressure conditions, the liquid does not flow out of the nozzle 14 because of its surface tension. The container 44 is connected to a transducer 50 of a piezoelectric type, capable of provoking, when excited, a sudden volume variation inside the container 44 and therefore a sudden pressure variation in the liquid present in it, such as to determine the flowing out of a calibrated jet of one or more drops through the nozzle 14. The transducer 50, which is placed very near to the nozzle 14 and housed for example in a small block 52 made of plastic material, is excited by means of a source of electrical pulses 54, which have the characteristics previously described, feeding of the transducer 50 on its electrodes 51, through a circuit 53 having a switch 55 by means of which the operator can close the circuit and then control the emission of the jet of drops. To the source 54 a known means 56 is connected to vary the amplitude of pulse or pulses communicated to the transducer 50; another component 57 is also connected, capable of controlling the duration of the pulse or series of pulses.

For operation, the container 44 must be filled with the liquid sample, possibly by means of a microsyringe, at least in its section close to the nozzle 14, and the transducer 50 is submitted to a pulse or series of pulses having a predetermined amplitude, during which, in correspondence with the nozzle 14, a jet of one or more drops of sample liquid is emitted, in a small pre-set table quantity. Said jet presents high directionality and an extremely limited increase in diameter, so that it can be directed into a column with one the systems which will be considered, for example through the injecton port of a direct injector, equipped with a "slice" type or rotative valve.

The amplitude of pulses may be regulated by the element 56, in order to obtain a corresponding regulation of the pressure increase provoked by said pulses and consequently of a first parameter affecting the operative conditions, in particular of the correct formation of the jet of drops, considering the nozzle diameter and the nature of the treated liquid. When the other conditions are kept unchanged, the ejected quantity of a given sample, thanks to the formation of a pulse having a preset amplitude, is exactly definite and equal to a drop, and therefore the ejected quantity obtained by a series of pulses will depend only on the duration of the latter and therefore on the number of pulses forming such series, because the time period of each pulse is determined by the transducer characteristics.

FIGS. 5 and 6 show the use of the injection apparatus in cold injection split or splitless gas-chromatography, for instance to carry out the method as depicted in the U.S. Pat. No. 4,383,839.

In this case, the injector body 70 shows a neck 72, which advantageously has an axial length as small as possible and on the two sides of which there are positioned a pre-column or vaporization chamber 66 and the container 10 or 12, the latter being preferably housed in the protecting collar 74, which provides for seating of said container 10 or 12 on the inner wall of the injector.

In this case, it is advisable, as already said, (i) that the distance between the outlet neck 14 or 16 of container 10 or 12 and the pre-column 66, as measured in an axial direction, be as small as possible, for instance 10 mm maximum, (ii) that the injection pressure of the jet into the neck 14 or 16 be sufficient for maintaining the latter in such a condition as to give rise to a very small opening angle of the jet, (iii) that the axial alignment of the neck 14 and pre-column 66 be perfect, and (iv) that a valve, f.i. a slide valve 70', be placed to close the injector duct when the injection device is not in position. It is particularly important in this case that, during injection, the carrier feeding, always according to arrows 68, be discontinued to avoid having the carrier gas drag the outside part of the injected sample, especially if the latter contains easily vaporizable substances. FIG. 7 diagrammatically shows the use of an injection apparatus as above described, in thin layer chromatography. The apparatus is the same as shown in FIG. 4 and the same components thereof are shown with the same reference numerals. The injector feeds a small volume of sample on a well known plate or dish 74 which is fixed when a radial elution is foreseen. As an alternative, the dish 74 and the injector body 52 may have a relative rectilinear movement, as shown by arrow 76 when a longitudinal elution in foreseen.

FIGS. 8 and 9 show an injection device as used in high pressure liquid chromatography. As well known, the injection device uses a valve with two bodies which can be axially rotated in order to put the same in at least two different positions, namely a load position and an injection position, as diagrammatically shown in the upper part and respectively in the lower part of FIG. 8. In the load position of valve 78, a pump connected at 80 feeds liquid under pressure to the column, which is connected at 82. A port for injecting the sample is shown at 84 and is connected with a loop 86 having its other end connected to the valve at 92. Ports 88 and 90 are connected to vents. In the load position the liquid from 80 enters the column in 82 and washes the same. A sample introduction is carried out at port 84. Then the valve is rotated in its injecting position and the liquid from 80 enters the valve, washes the loop 86 and injects the sample in the column. In this case too it is important to have very small sample volumes and to this end the sample introduction at port 84 can be carried out as depicted in FIG. 9 by means of a device 12-74 of the type of that shown in FIG. 6. The valve 94 has a stator 102 and a rotor 94 with a rotor seal 98 therebetween. A duct 104 with an interposed seal 100 crosses the three elements 94, 98 and 102 when the valve is in its load position. A slice valve 96 closes an enlarged outer part of duct 104, wherein the device 12-74 can be removably housed to inject a calibrated sample small volume within the duct 104 until reaching the loop 86. Of course other types of devices, for instance similar to that of FIG. 4 or that of FIG. 5 can be used.

Finally, it should also be noticed that the embodiments of the present invention as above illustrated and described can be submitted to several changes and variations without departing from the spirit and scop of the invention itself, these variations comprising the use of an automatic sampler, wherein the container is automatically filled and wherein sample emission occurs through several jets of sample.

We claim:

1. An apparatus for volumetrically controlled and reproducible injection of small quantities of liquid sample into a chromatographic system, comprising, in combination with an injection device for a chromatographic system;

a sample container having a volume greater than a desired liquid sample volume and having a pipette- or nozzle-shaped neck at its outlet, terminating in an opening with a diameter of 1–100 μm;

positioning means for operatively positioning said sample container in a sample injection device of a chromatographic system, for injection of a sample through said outlet opening; and pulse means communicating with said container for applying to a liquid inside the container at least one pressure pulse of controlled amplitude and duration, and ending in an abrupt pressure drop; wherein said pulse means comprises at least one transducer capable of producing at least one pressure pulse of high amplitude and short duration in the sample container; a pulse source for exciting said transducer; and means for adjusting at least one of the amplitude or the number of the pulses.

2. An apparatus according to claim 1, wherein said injection device is a gas chromatography injection device comprising a cold sample split-splitless sampling system in which the vaporizing chamber is maintained cold during the liquid injection and thereupon heated to vaporize the sample.

3. An apparatus according to claim 1, wherein said injection device is used to deposit the sample on thin layer chromatography plate.

4. An apparatus according to claim 1 wherein said injection device is a high resolution liquid chromatography injection device of the valve type containing a loop with a larger volume in which the small sample size is injected.

5. An apparatus according to claim 1, wherein said transducer is a piezoelectric transducer, and said pulse source is a source of electric pulses of high amplitude and steep dropoff.

6. An apparatus according to claim 5, wherein said sample container is made of glass or fused silica and is surrounded, near the outlet opening thereof, by a piezoelectric transducer embedded in a small block of a plastic material.

7. An apparatus according to claim 1, wherein the sample container has at least a part thereof made of nickel in the portion containing the liquid sample; wherein the transducer comprises a magnetostrictive device capable of acting on said container part when in its operative position within a seat provided in said magnetostrictive device, and actuating means for applying to said magnetostrictive device at least one current pulse having an adjustable amplitude, thereby producing a corresponding pressure pulse acting on the liquid contained in the nickel part of said container.

8. An apparatus according to claim 7, wherein said pulse has a duration which depends on the frequency of mechanical resonance of the magnetostrictive device and is adjustable in amplitude.

9. An apparatus according to claim 1, wherein the diameter of the sample container outlet opening is 1–30 μm.

* * * * *

UNITED STATES PATENT AND TRADEMARK OFFICE
CERTIFICATE OF CORRECTION

PATENT NO. : 4,526,686
DATED : July 2, 1985
INVENTOR(S) : GIORGIO SISTI ET AL

It is certified that error appears in the above-identified patent and that said Letters Patent is hereby corrected as shown below:

Title page, second inventor: read "Sorin Trestiano"

should read -- Sorin Trestianu --.

Signed and Sealed this

Fifteenth Day of October 1985

[SEAL]

Attest:

Attesting Officer

DONALD J. QUIGG

Commissioner of Patents and
Trademarks—Designate